US00PP34455P2

(12) United States Plant Patent
Spil

(10) Patent No.: US PP34,455 P2
(45) Date of Patent: Jul. 26, 2022

(54) ***ECHINACEA* PLANT NAMED 'IFECSSWP'**

(50) Latin Name: *Echinacea hybrida*
Varietal Denomination: 'IFECSSWP'

(71) Applicant: INNOFLORA PLANT BREEDING B.V., Heerhugowaard (NL)

(72) Inventor: Glenn Spil, Zuidermeer (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 17/563,981

(22) Filed: Dec. 28, 2021

Related U.S. Application Data

(60) Provisional application No. 63/133,902, filed on Jan. 5, 2021.

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Echinacea* plant named 'IFECSSWP', characterized by its upright and relatively compact plant habit; moderately vigorous growth habit; freely branching habit; strong flowering stems; numerous and large single-type inflorescences with four whorls of white-colored ray florets and greenish yellow-colored receptacle spines; and good garden performance.

2 Drawing Sheets

Figure 1:
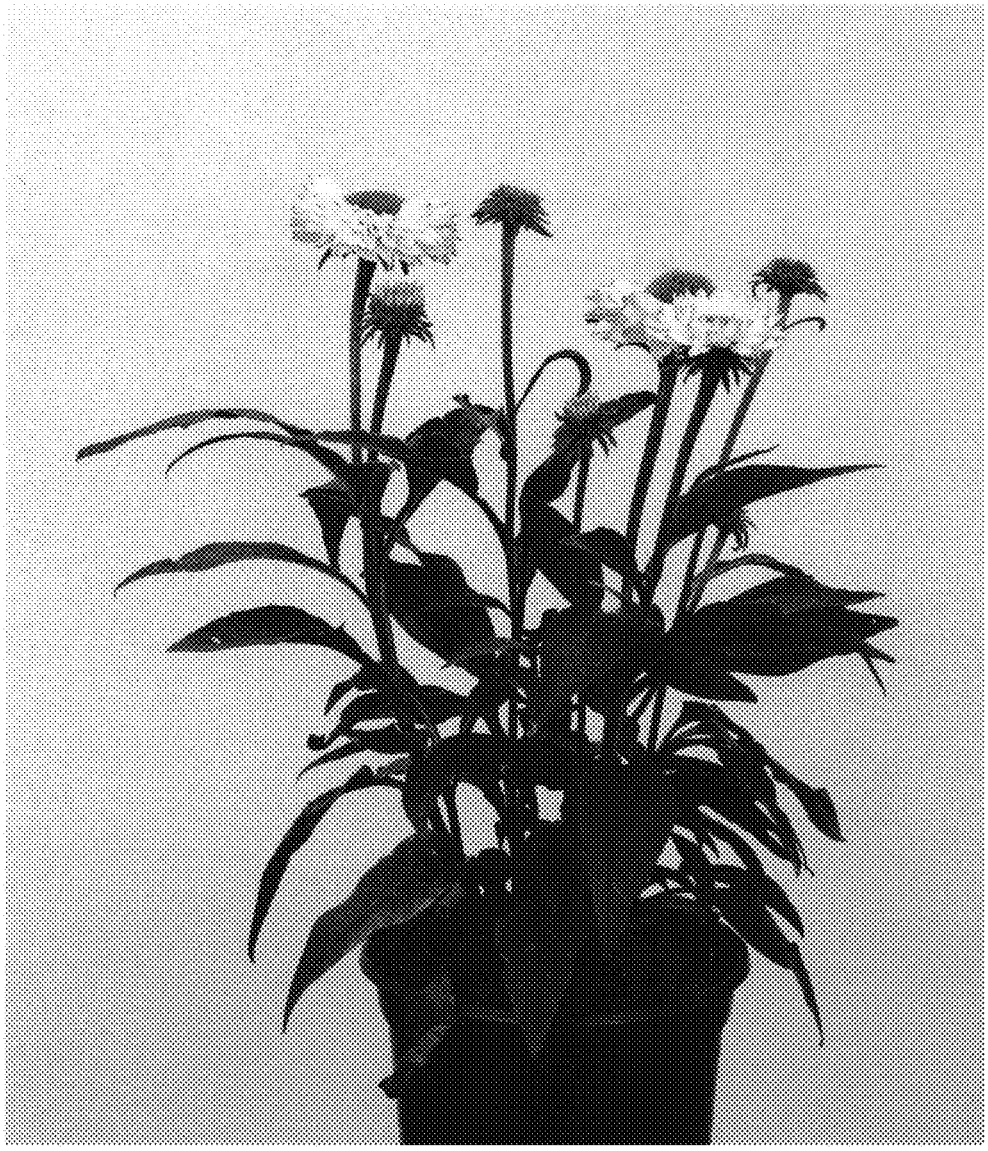

Botanical designation: *Echinacea hybrida.*
Cultivar denomination: 'IFECSSWP'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Innoflora Plant Breeding B.V. of Heerhugowaard, The Netherlands on Nov. 6, 2020, application number 2020/2810. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Echinacea* plant, botanically known as *Echinacea hybrida*, and hereinafter referred to by the name 'IFECSSWP'.

The new *Echinacea* plant is a product of a planned breeding program conducted by the Inventor in Heerhugowaard, The Netherlands. The objective of the breeding program is to develop new vigorous and freely flowering *Echinacea* plants with large inflorescences with unique and attractive ray floret coloration.

The new *Echinacea* plant originated from a cross-pollination in July, 2017 in Heerhugowaard, The Netherlands of a proprietary selection of *Echinacea hybrida* identified as code number 009-15-K010-04, not patented, as the female, or seed, parent with a proprietary selection of *Echinacea hybrida* identified as code number 009-15-K010-02, not patented, as the male, or pollen, parent. The new *Echinacea* plant was discovered and selected by the Inventor as a single flowering plant from within the progeny of the stated cross-pollination grown in a controlled greenhouse environment in Heerhugowaard, The Netherlands in August, 2018.

Asexual reproduction of the new *Echinacea* plant by in vitro meristem culture in a controlled environment in Heerhugowaard, The Netherlands since September, 2018 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'IFECSSWP'. These characteristics in combination distinguish 'IFECSSWP' as a new and distinct *Echinacea* plant:

1. Upright and relatively compact plant habit.
2. Moderately vigorous growth habit.
3. Freely branching habit.
4. Strong flowering stems.

5. Numerous and large single-type inflorescences with four whorls of white-colored ray florets and greenish yellow-colored receptacle spines.
6. Good garden performance.

Plants of the new *Echinacea* can be compared to plants of the female parent selection. Plants of the new *Echinacea* differ primarily from plants of the female parent selection in the following characteristics:

1. Plants of the new *Echinacea* are more compact than plants of the female parent selection.
2. Inflorescences of plants of the new *Echinacea* have more whorls of ray florets than inflorescences of plants of the female parent selection.
3. Plants of the new *Echinacea* and the female parent selection differ in ray floret color as plants of the new *Echinacea* have white-colored ray florets whereas plants of the female parent selection have light yellow-colored ray florets.

Plants of the new *Echinacea* can be compared to plants of the male parent selection. Plants of the new *Echinacea* differ primarily from plants of the male parent selection in the following characteristics:

1. Plants of the new *Echinacea* are taller than plants of the male parent selection.
2. Inflorescences of plants of the new *Echinacea* have more whorls of ray florets than inflorescences of plants of the male parent selection.
3. Plants of the new *Echinacea* and the male parent selection differ in ray floret color as plants of the new *Echinacea* have white-colored ray florets whereas plants of the male parent selection have light yellow-colored ray florets.

Plants of the new *Echinacea* can be compared to plants of *Echinacea purpurea* 'Virgin', disclosed in U.S. Plant Pat. No. 18,684. In side-by-side comparisons, plants of the new *Echinacea* differ primarily from plants of 'Virgin' in the following characteristics:

1. Plants of the new *Echinacea* are more compact than plants of 'Virgin'.
2. Inflorescences of plants of the new *Echinacea* have more whorls of ray florets than inflorescences of plants of 'Virgin'.

Plants of the new *Echinacea* can also be compared to plants of *Echinacea hybrida* 'Meditation White', disclosed in U.S. Plant Pat. No. 27,015. In side-by-side comparisons, plants of the new *Echinacea* differ primarily from plants of 'Meditation White' in the following characteristics:

1. Plants of the new *Echinacea* have larger leaves than plants of 'Meditation White'.
2. Inflorescences of plants of the new *Echinacea* have more whorls of ray florets than inflorescences of plants of 'Meditation White'.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet (FIG. 1) is a side perspective view of a typical flowering plant of 'IFECSSWP' grown in a container.

Figure 2:
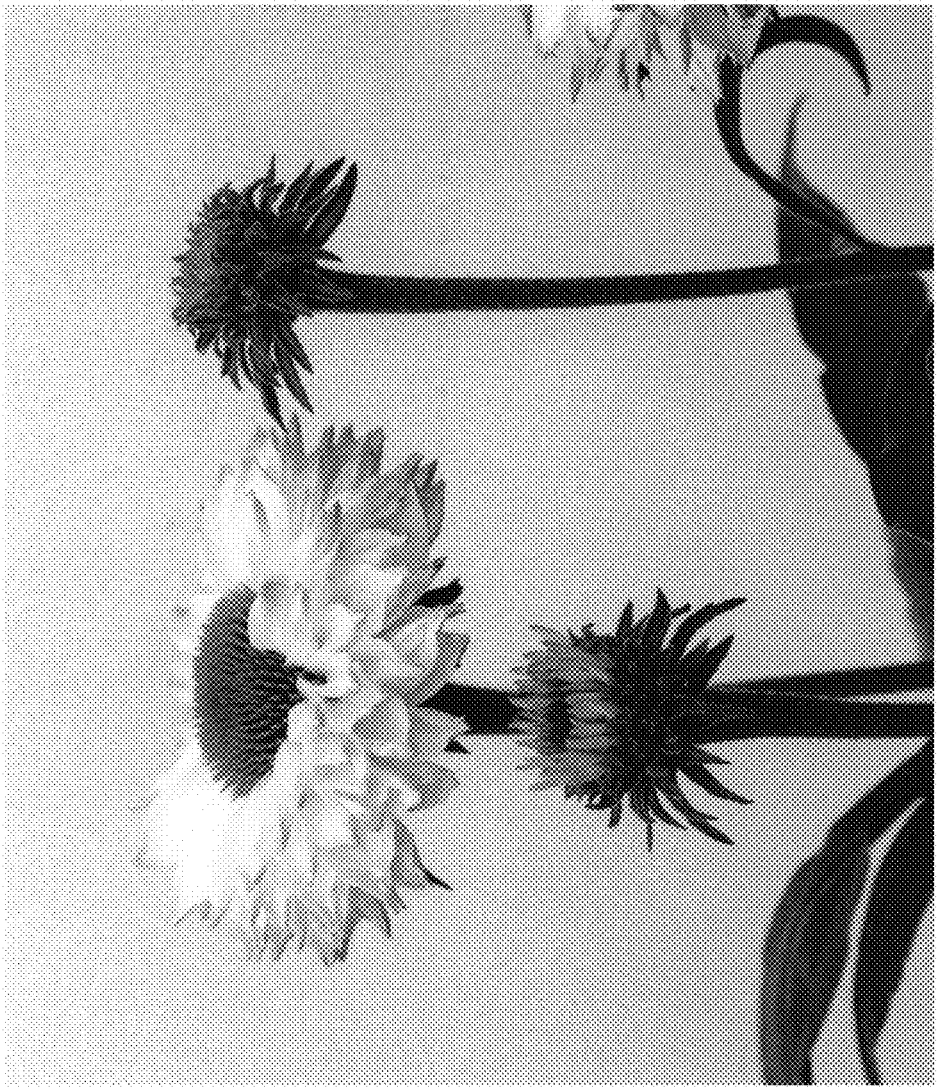

The photograph on the leaf side of the second sheet (FIG. 2) is a close-up view of typical inflorescences of 'IFECSSWP'.

Figure 3:
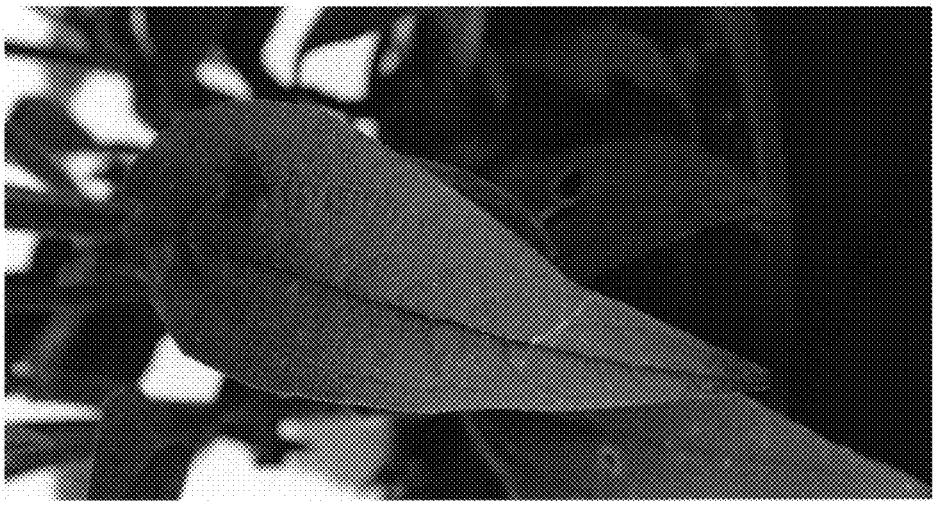

The photograph on the right side of the second sheet (FIG. 3) is a close-up view of typical leaves of 'IFECSSWP'.

DETAILED BOTANICAL DESCRIPTION

The aforementioned photographs and following observations and measurements describe plants grown during the late summer in 17-cm containers in an outdoor nursery in Heerhugowaard, The Netherlands and under cultural practices typically used in commercial *Echinacea* production. During the production of the plants, day temperatures ranged from 16° C. to 30° C. and night temperatures ranged from 8° C. to 18° C. Plants were pinched eight weeks after planting and were two years old when the photographs and description were taken. In the following description, color references are made to The Royal Horticultural Society Colour Chart, 2015 Edition, except where general terms of ordinary dictionary significance are used.

Botanical classification: *Echinacea hybrida* 'IFECSSWP'.

Parentage:

*Female parent.*—Proprietary selection of *Echinacea hybrida* identified as code number 009-15-K010-04, not patented.

*Male parent.*—Proprietary selection of *Echinacea hybrida* identified as code number 009-14-K010-02, not patented.

Propagation:

*Type.*—By in vitro meristem culture.

*Time to initiate roots, summer.*—About twelve days at temperatures about 20° C.

*Time to initiate roots, winter.*—About 16 days at temperatures about 20° C.

*Time to produce a rooted young plant, summer.*—About 36 days at temperatures about 18° C.

*Time to produce a rooted young plant, winter.*—About 42 days at temperatures about 18° C.

*Root description.*—Thick, fleshy; typically white in color, actual color of the roots is dependent on substrate composition, water quality, fertilizer type and formulation, substrate temperature and physiological age of roots.

*Rooting habit.*—Moderately freely branching; sparse.

Plant description:

*Plant form and growth habit.*—Herbaceous perennial; upright and relatively compact plant habit, inverted triangle; freely basal branching habit with about eight primary lateral branches developing per plant; moderately vigorous growth habit and moderate growth rate.

*Plant height.*—About 39.5 cm.

*Plant diameter or spread.*—About 38.5 cm.

*Lateral branches.*—Length: About 20.3 cm. Diameter: About 5 mm. Internode length: About 4.5 cm. Aspect: Erect to about 15° from vertical. Strength: Strong. Texture: Densely pubescent; strigose, rough. Color: Close to 144A.

Leaf description:

*Basal leaves.*—Arrangement: Alternate, simple. Length: About 14.7 cm. Width: About 4.6 cm. Shape: Ovate to narrowly ovate. Apex: Acute to narrowly acute. Base: Attenuate. Margin: Entire; not undulate. Texture and luster, upper and lower surfaces: Moderately to densely pubescent, strigose and rough; matte. Venation pattern: Pinnate. Color: Developing leaves, upper surface: Close to 137B. Developing leaves, lower surface: Close to 146B. Fully expanded leaves, upper surface: Slightly darker than NN137A and 147A; venation, close to 144A. Fully expanded leaves, lower surface: Slightly darker than 147B; venation, close to 145B.

*Cauline leaves.*—Arrangement: Alternate, simple. Length: About 11.9 cm. Width: About 4.1 cm. Shape: Ovate to narrowly ovate. Apex: Acute to narrowly acute. Base: Attenuate. Margin: Entire; not undulate. Texture and luster, upper and lower surfaces: Moderately to densely pubescent, strigose and rough; matte. Venation pattern: Pinnate. Color: Developing leaves, upper surface: Close to 137B. Developing leaves, lower surface: Close to 146B. Fully expanded leaves, upper surface: Slightly darker than NN137A and 147A; venation, close to 144A. Fully expanded leaves, lower surface: Slightly darker than 147B; venation, close to 145B.

*Petioles, basal leaves.*—Length: About 5.1 cm. Diameter: About 3.25 mm by 4 mm. Texture, upper surface: Smooth, glabrous; margins, moderately pubescent. Texture, lower surface: Moderately pubescent. Color, upper surface: Close to NN137A; midvein, close to N144A. Color, lower surface: Close to 137B; midvein, close to 145A.

*Petioles, cauline leaves.*—Length: About 2.6 cm. Diameter: About 3.25 mm by 4 mm. Texture, upper surface: Smooth, glabrous; margins, moderately pubescent. Texture, lower surface: Moderately pubescent. Color, upper surface: Close to NN137A; midvein, close to N144A. Color, lower surface: Close to 137B; midvein, close to 145A.

Inflorescence description:

*Appearance.*—Large single-type inflorescences with ray and disc florets arranged on a capitulum; inflorescences positioned upright above the foliar plane on mostly upright and strong peduncles.

*Flowering habit.*—Freely flowering habit with about 16 developing and fully developed inflorescences per plant.

*Fragrance.*—Moderately to strongly fragrant; sweet and pleasant.

*Time to flower.*—Plants flower continuously from early July to late September in The Netherlands.

*Inflorescence longevity.*—Inflorescences maintain good substance for about three weeks on the plant; inflorescences persistent.

*Inflorescence buds.*—Height: About 3 cm. Diameter: About 2.9 cm. Shape: Flattened globular. Color: Slightly darker than 143A.

*Inflorescence size.*—Diameter: About 8.4 cm. Depth (height): About 4 cm. Disc diameter: About 3.6 cm.

*Receptacles.*—Height: About 1.1 cm. Diameter: About 1.3 cm. Shape: Broadly ovate. Color: Close to 157D.

*Ray florets.*—Quantity and arrangement: About 100 arranged in about four whorls at the base of the receptacle. Length: About 3.1 cm. Width: About 1.2 cm. Shape: Elliptic to obovate; moderately carinate. Apex: Emarginate to praemorse. Base: Cuneate. Margin: Entire. Texture and luster, upper surface: Smooth, glabrous; velvety; matte. Texture and luster, lower surface: Densely pubescent; slightly glossy. Aspect: About 75° from vertical to horizontal. Color: When opening, upper surface: Close to 155C and at the apex, close to 145C. When opening, lower surface: Close to 155A and at the apex, close to 145B to 145C. Fully opened, upper surface: Close to 155C and at the apex, close to 145C to 145D; venation, similar to lamina; color does not change with subsequent development. Fully opened, lower surface: Close to 155A and at the apex, close to 145C; venation, similar to lamina; color does not change with subsequent development.

*Disc florets.*—Quantity and arrangement: About 300 per inflorescence, arranged spirally at the center of the inflorescence. Length: About 1.1 cm. Diameter: About 2 mm. Shape: Tubular; proximally, 15% free, not fused. Apex: Acute. Base: Fused. Margin, free-part: Entire. Texture and luster, inner and outer surfaces: Smooth, glabrous; moderately glossy. Color, when opening, inner and outer surfaces: Apex: Close to 143B. Mid-section: Close to 145D. Base: Close to 150C. Color, fully opened, inner and outer surfaces: Apex: Close to 144A. Mid-section: Closes to 145D. Base: Close to 144C.

*Receptacle spines.*—Quantity: One per disc floret; about 300 per inflorescence. Shape: Acicular. Apex: Acute. Base: Attenuate. Texture and luster: Smooth, glabrous; glossy. Color: Apex: Close to 153C. Mid-section: Close to 143B. Base: Close to 145D.

*Involucral bracts.*—Quantity per inflorescence: About 100 arranged in about four whorls. Length: About 1.2 cm. Width: About 2.5 mm. Shape: Narrowly ovate; moderately reflexed. Apex: Acute. Base: Cuneate. Margin: Entire. Texture and luster, upper surface: Smooth, glabrous; slightly glossy. Texture, lower surface: Densely pubescent. Color, upper surface: Close to NN137A. Color, lower surface: Close to NN137C.

*Peduncles.*—Length: About 13.7 cm. Diameter: About 4.5 cm. Strength: Strong. Aspect: Mostly upright. Texture: Densely pubescent; strigose. Color: Close to 144A and 145A.

*Reproductive organs.*—Androecium (present on ray and disc florets): Quantity per floret: Five. Filament length: About 4 mm. Filament color: Close to 157D. Anther length: About 3 mm. Anther shape: Lanceolate. Anther color: Close to 200A to slightly darker than 200A. Pollen amount: Scarce. Pollen color: Close to 21A. Gynoecium (present only on disc florets): Quantity per floret: One. Pistil length: About 7 mm. Stigma shape: Decurrent, unequal. Stigma color: Close to 153C. Style length: About 6 mm. Style color: Close to 154D. Ovary color: Close to 145D. Seeds and fruits: To date, seed and fruit development have not been observed on plants of the new *Echinacea*.

Pathogen & pest resistance: To date, plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'IFECSSWP' as illustrated and described.

* * * * *